United States Patent [19]

Joo

[11] Patent Number: 4,562,147
[45] Date of Patent: Dec. 31, 1985

[54] METHOD AND KIT FOR DIAGNOSIS OF PSEUDORABIES

[75] Inventor: Han S. Joo, St. Paul, Minn.

[73] Assignee: Regents of the University of Minnesota, Minneapolis, Minn.

[21] Appl. No.: 503,824

[22] Filed: Jun. 13, 1983

[51] Int. Cl.$^4$ .................. C12Q 1/70; G01N 33/54; B65D 71/00

[52] U.S. Cl. .................................. 435/5; 435/7; 435/810; 436/514; 436/515; 436/807; 436/808; 436/809

[58] Field of Search ................ 435/5, 7; 436/514, 515

[56] References Cited

U.S. PATENT DOCUMENTS 4,470,967  9/1984  Gough et al. .................. 424/89

FOREIGN PATENT DOCUMENTS

WO84/1289  12/1984  PCT Int'l Appl. .................. 424/89

OTHER PUBLICATIONS

Yen et al., Chem. Abstracts, 97(1982), 21812j.

*Primary Examiner*—Christine M. Nucker
*Attorney, Agent, or Firm*—Burd, Bartz & Gutenkauf

[57] ABSTRACT

A radial immunodiffusion enzyme assay method for the simple testing of pseudorabies antibodies in swine and other animals. Agar test plates are provided including an underlying adherent coating of solubilized non-infectious swine pseudorabies antigen. Blood or blood serum samples from affected animals are placed in wells punched in the agar layer and allowed to incubate overnight. The agar gel is then removed. The resulting antigen layer with bound antibodies from the samples is washed and reacted with enzyme conjugated anti-swine immunoglobulin. The reaction is visualized by overlaying the bound conjugate layer with agar containing a color producing enzyme substrate. The diameters of resulting colored zones are correlated with the titers obtained by the official virus neutralization test. Methods of preparing antigen and antigen coated test plates are disclosed along with testing kits for carrying out the test procedure in the field.

19 Claims, 5 Drawing Figures

METHOD AND KIT FOR DIAGNOSIS OF PSEUDORABIES

BACKGROUND OF THE INVENTION

1. Field of the Invention

Pseudorabies is a fatal and economically important disease in swine. Because the incidence and severity have increased during recent years, a strict quarantine is required by law on all infected herds. Any movement of breeding pigs, except to slaughter, is required to be negative of infection by serological test. A simple, reliable and rapid testing method in the field, which can be applied by veterinarians without special facilities or skills, is needed.

This invention relates to a method and test kit which have such advantages and will contribute to the control of this worldwide disease in which early detection and elimination of the infected animals are important in the control. More particularly, this invention relates to a radial immunodiffusion enzyme assay technique and kit for the diagnosis of pseudorabies in swine by the detection of antibodies to pseudorabies virus. The technique is simple and inexpensive to perform and gives the results overnight. Because of its simplicity the test can be carried out on the farm by persons with little laboratory experience. Although pseudorabies affects other species, such as cattle, sheep and dogs, and the test disclosed can be used to diagnose the disease in them, the greatest present interest is in swine and the invention is described with particular reference to swine.

2. The Prior Art

Several techniques are available to test for pseudorabies virus antibodies. The virus neutralization test has been approved as the official method in the United States. However, for the virus neutralization test each sample must be sent to a laboratory which has facilities for tissue culture and techniques to conduct the test. The cost per sample is high. Obtaining the results requires 72 hours plus mailing time. Total time often exceeds 7 days. Other available tests include immunofluorescence, enzyme-linked immunosorbent assay (ELISA), agar gel immunodiffusion, complement fixation, indirect hemagglutination and skin tests. However, none of them is both easy to perform in the field and reliable. Details of each technique are described by Gustafson, Chapter 14, "Pseudorabies" in *Diseases of Swine*, edited by A. D. Leman et al, 1981, Iowa State University Press.

Although the basic principles of radial immunodiffusion enzyme assay are known and have been used for other purposes (Elwing et al, *Journal of Immunological Methods*, Vol. 39, pp. 247-56, 1980), the basic technique has been modified and adapted in order to permit testing of pseudorabies virus antibodies. Intact pseudorabies virus particles neither adhere to the test plate reproducibly nor react in the test with high reproducibility, sensitivity and specificity. The design has been improved by chemical treatment of infected cellular pseudorabies virus antigen. This is a significant step in eliminating the contamination of infectious virus in the environment and increasing the specificity of test reaction. Following infection, protective antibodies are directed against the envelope protein of pseudorabies virus, the antigen used in carrying out the present invention. Herein the viral component involved in protective immunity is specifically identified, rather than virus reactive or virus associated antigens. The manner of application of antigen to a test plate forming an integral part of the test kit has been modified to insure consistent binding of the antigen to the plate surface.

SUMMARY OF THE INVENTION

According to this invention, a pseudorabies virus-specific antigen is first prepared. Cell monolayers are infected with pseudorabies virus and incubated. The infected cells are collected and solubilized in the presence of chemical detergents. After removing cell debris by high speed centrifugation, the supernatant is used for antigen. An optimal concentration of the solubilized antigen diluted in a coating buffer is adsorbed on a supporting surface (e.g., petri dish) that has preferably been prewashed, as with ethanol. The antigen coating may be further treated by applying a solution of any protein fixative agent, such as 1% formaldehyde or 0.5% glutaraldehyde to add shelf life to the test plates. The antigen coating is preferably fixed by applying a bovine serum albumin or gelatin in solution. A relatively thick layer of 1% agar, which agar solution may incorporate a preservative agent, such as 0.01% sodium azide, is applied and permitted to solidify. At least one test sample receiving well is formed by removing a plug of the agar layer. The resulting test plate is prepared in advance of need and forms part of a diagnostic kit for detection of pseudorabies.

On the farm or in the feedlot, personnel, such as veterinarians, will test with blood or blood serum samples drawn from swine by filling the samples into the wells of the test plate and incubating at room temperature (10°-30° C.) overnight (12-24 hours). The pseudorabies antibodies in the test sample diffuse out into the agar at a rate proportional to their concentration in the sample and become bound to the antigen layer during the incubation period. The agar gel layer then is removed. The antigen-antibody layer is washed, preferably with washing buffer. An enzyme conjugated anti-swine immunoglobulin antibody is applied to the antigen-antibody layer and incubated and that layer is again washed, preferably with the washing buffer. A further agar layer mixed with an enzyme substrate is applied over the washed antigen-antibody-conjugate layer. A reaction occurs between the substrate in the agar layer and conjugate producing a colored ring within a few minutes. The diameter of the ring, which is proportional to the concentration of antibodies, is measured and the antibody quantity is interpreted by a standard reference table related to the initial sample size. Based upon the determination of the antibody status of pseudorabies virus in the tested swine, the infected hogs may be selected for disposal as part of eradication of the disease in the herd.

The components used in carrying out the test procedure are preferably prepared and packaged as a kit. These include pre-prepared antigen coated-agar test plates, concentrated washing solution, conjugated antibody, agar, enzyme substrate and positive and negative control sera.

BRIEF DESCRIPTION OF THE DRAWINGS

The invention is illustrated schematically in the accompanying drawings in which the same numerals refer to corresponding parts and in which.

DETAILED DESCRIPTION OF THE PREFERRED EMBODIMENT

Preparation of Antigen

Antigen for use in production of test plates for detection of pseudorabies virus antibodies is prepared as follows: Pig kidney cells are grown to a confluent monolayer in Dulbecco's Modified Eagle's Medium (DMEM) supplemented with 5% fetal bovine serum. After confluence is reached, the medium is removed and pseudorabies virus is inoculated. Following incubation at 37° C. for one hour, serum-free DMEM is added. When the infected monolayers show maximum cytopathic effect (12-24 hours), the cells are scraped off and centrifuged at 3,000 rpm for ten minutes at 4° C. The supernatant medium is discarded. The cells are suspended in Tris buffer containing a chemical detergent such as 0.5% Triton X-100. Alternatively, other Triton detergents, NP-40, sodium deoxycholate (0.05-2%), sodium dodecylsulfate (0.5-2%), low molecular weight polysorbic acids, sodium thiolyate, and the like, may be used. The cell suspension is stirred at 4° C. for 1½ hours during which time the viral envelope is solubilized, and rises to the surface of the solution. The solution is centrifuged at 4° C. for 60 minutes at 10,000 rpm to bring down the cells. The supernatant fluid is decanted from the cellular debris and used to prepare the antigen layer of test plates. This preparation can be diluted 100 to 1000 times without losing sensitivity. It may be stored at −70° C.

Preparation of Test Plates

Figure 1:
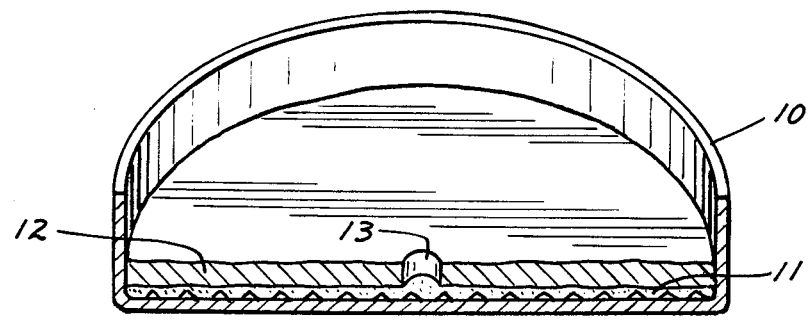
FIG. 1 is a perspective view, partly in vertical section, of a petri dish test plate.

Test plates are prepared by initially applying a layer of pseudorabies virus antigen to a suitable supporting surface. Preferably polystyrene or glass petri dishes 10 (FIG. 1) or similar flat receptacles are used for this purpose. The supporting surface is preferably washed with ethanol. After drying, a solution of pseudorabies virus antigen is applied to the clean surface and allowed to adsorb for from about 2 to 4 hours to overnight. The antigen is diluted to an optimum concentration between about 0.01 to 0.001%, preferably in a sodium bicarbonate-sodium carbonate coating buffer to promote adherence of the antigen coating 11 to the supporting surface. The coating buffer should preferably be between about 0.01M to 0.1M (pH 9 to 10) containing from about 0.84 to 8.4 grams per liter of $NaHCO_3$ and 0.11 to 10.6 grams per liter of $Na_2CO_3$. After formation of the adsorbed antigen layer 11, the excess solution is poured off. The antigen coating 11 may be washed with distilled water. Preferably a fixation layer such as bovine serum albumin in solution is applied over the antigen coating and the excess is poured off. A melted agar layer 12 is applied and permitted to solidify. The depth of the agar layer is not critical. It should be at least about 1.5 mm and preferably about 2 mm up to about 10 mm. The agar layer is applied from solution between about 0.75 to 1.5% and preferably about 1%. At least one, and preferably a plurality of small diameter holes 13, are punched out of the solid agar to function as test sample wells. The wells may be about 1 to 4 mm in diameter, for example, and penetrate through the agar coating. The prepared test plates are maintained clean and moist by being kept covered until ready for use. They may be sealed, for example, in a non-pervious foil or plastic pouch.

Testing Procedure

A measured amount of whole blood or blood serum from an animal to be tested is placed in a well of a test plate. Preferably a sample of 15 μl is used when the well diameter is 2 mm. Preferably positive and negative controls are provided to be run with each set of tests. The same amount of control serum is placed in other wells on the test plate. The test sample is allowed to diffuse and react overnight at room temperature. For precise results, the incubation time should be 17 hours for blood samples and 15 hours for serum samples. For approximate results, the plates may be incubated for between about 12 and 24 hours. During incubation the test serum or blood added to the wells radially diffuses through the agar proportionately to the concentration of virus antibodies in the test samples and in the animals from which the samples are taken and pseudorabies specific antibodies bind to the antigen.

Figure 2:
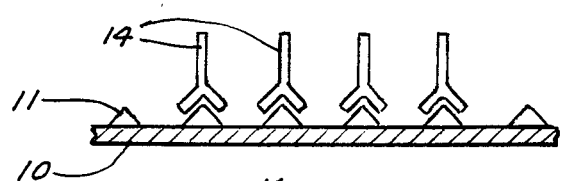
FIG. 2 shows schematically, on a greatly enlarged scale, the binding of test sample antibodies to antigen.

After incubation of the plates, the agar gel layer is peeled off and the plates are washed, preferably with a washing buffer such as Tween 20 in phosphate buffered saline. Plates may be washed with distilled or tap water rather than washing buffer. Such a wash is not as effective, in that there will be a somewhat darker background and some tiny spots, features which interfere with the aesthetic appearance but not the utility of the test. Washing removes unbound (non-specific) antibodies. As seen schematically in FIG. 2, the antibodies 14 that have reached the antigen layer 11 are bound to it. Antigen layer 11 in turn adheres to the supporting surface 10.

Figure 3:
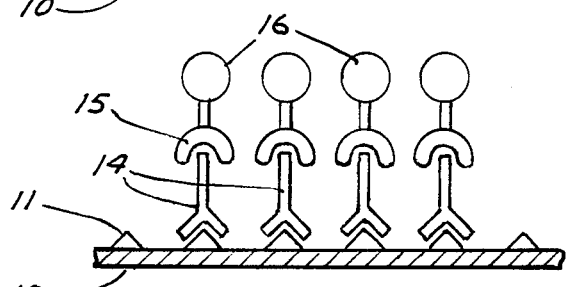
FIG. 3 similarly shows schematically the binding of conjugated anti-swine immunoglobulin antibody to the test sample antibodies.

A conjugate in the form of a species specific-enzyme linked anti-immunoglobulin is applied to the test plate. Specifically, the conjugate is an anti-swine immunoglobulin having an enzyme chemically bound (conjugated) to it. As seen schematically in FIG. 3, the immunoglobulin 15 with bound enzyme 16 binds to the antibodies 14 adhering to the antigen layer. The conjugate is diluted. Although a special diluent is not needed, the conjugate is diluted preferably with a buffer such as Tween 20 in phosphate buffered saline. Alternatively, phosphate buffered saline with bovine serum albumin, or even water, may be used.

The enzyme can be any one of a number which react with a substrate to produce a colored compound. For example, peroxidase, such as that obtained from horseradish, produces a purple color when reacted with aminosalicylic acid and hydrogen peroxide, or p-phenylene diamine and hydrogen peroxide. Alkaline phosphatase produces a yellow color when reacted with dinitrophenylphosphate. Beta-galactosidase reacts with O-nitrophenyl-β-D-galactopyranoside to give a purple color.

Conjugates are commercially available. Most are made in the goat or rabbit. Peroxidase conjugated rabbit anti-swine immunoglobulins obtained from Miles Laboratories have been used.

The conjugate applied to the antibodies is maintained for about 30 minutes to 2 hours at room temperature. The plates are then washed, preferably with buffered washing solution to remove any unbound conjugate. Preferably the washing liquid is added slowly from the edge of the test plate with a syringe or pipette and poured off. This should desirably be repeated three times.

While the conjugate is incubating, a second agar coating is prepared. A 1% solution of agar, preferably in phosphate buffered saline, is melted and a substrate for the enzyme of the conjugate is incorporated. A catalyst is incorporated as needed. For example, when the enzyme is a peroxidase, the 1% agar solution may contain between about 0.05 to 0.10% of 5-aminosalicylic acid as the substrate and between about 0.002 and 0.01% hydrogen peroxide as catalyst, and preferably about 0.08% substrate and 0.005% catalyst.

Figure 4:
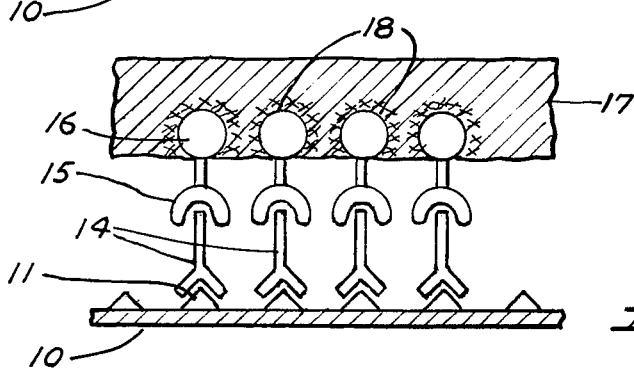
FIG. 4 similarly shows schematically an applied enzyme substrate-containing agar layer and development of a colored reaction product therein.
Figure 5:
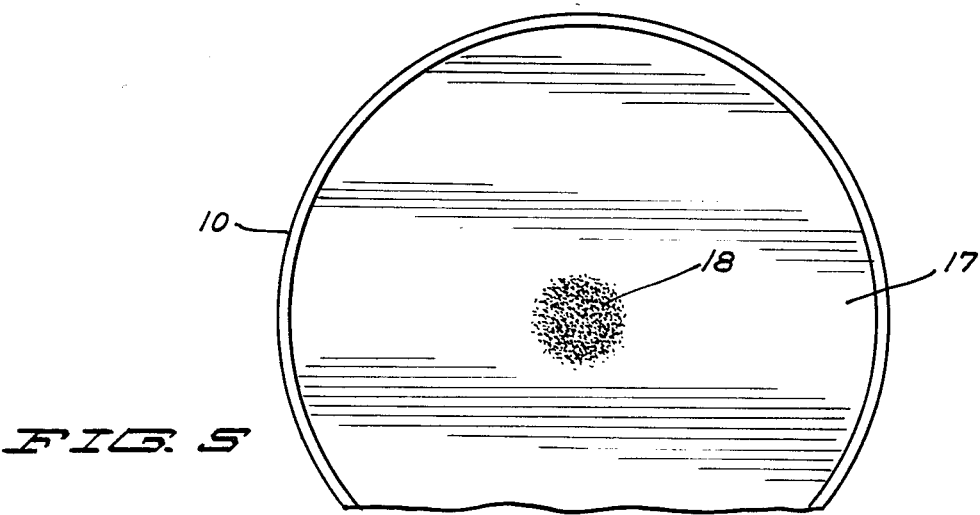
FIG. 5 is a plan view of a petri dish test plate showing schematically the formation of a colored ring for assay evaluation.

The agar is poured over the washed conjugate and allowed to solidify. As shown schematically in FIG. 4, a color reaction between the enzyme 16 of the conjugate occurs within the agar support layer 17, as shown at 18. As shown in FIG. 5, the color develops in the form of a circular zone or ring. The rings are dark enough to measure within about 10 to 20 minutes of the substrate reaction. Upon standing, the ring will become darker but will not become larger. The diameter of the ring produced is related to the amount of specific antibody present in the blood (i.e., virus neutralization titer). The diameter of the dark colored circular zone is measured and used to correlate with the standard virus neutralization test antibody value.

The values determined are related to the size of the sample well in the test plate and the size of the sample used. A table of values and/or depictions of representative rings are included in each test kit. The following table is representative of values resulting from the use of test plates having 2 mm diameter sample wells and 15 $\mu$l samples, allowed to diffuse for 15 hours (serum) or 17 hours (blood):

| Ring Diameter (mm) | Approximate Ranges of Neutralization Titer |
|---|---|
| <5.0 | Negative (<1:2) |
| 7.0–8.0 | 1:2–4 |
| 8.0–9.0 | 1:4–8 |
| 9.0–10.0 | 1:8–16 |
| 10.0–11.0 | 1:16–32 |
| >11.0 | >1:32 |

The agar layer bearing the colored ring may be removed and dried and maintained as a permanent record of the test. If the tested swine is free of antibodies to pseudorabies virus, the result is negative. If the swine is infected, antibodies are produced and the degree of severity of the disease is indicated. Sero positive reactions include three categories: (1) following natural virus infection, (2) vaccination, or (3) passive transfer, as for nursing pigs. Thus the test can be used for monitoring the immune status.

For ease of administration of the diagnostic test in the field, the materials are preferably assembled in a kit. Such a kit includes previously prepared test plates, solid agar, concentrated washing solution, conjugate, substrate, catalyst, positive and negative control serums, instructions for use including a table or chart for interpretation of the results. The size and quantity of the components depends upon the size of the herd to be treated. A typical kit for testing 26 samples, along with a positive and negative control, includes 4 antigen coated agar plates in 60 mm polystyrene petri dishes, each with 7 wells, 20 mls concentrated washing solution, 1 vial conjugate, 25 mls 1% agar, 1 vial substrate, 1 vial hydrogen peroxide, and 1 vial each of positive and negative control serum.

The invention is further illustrated by the following examples:

EXAMPLE 1

Preparation of the antigen

Swine kidney cells (PK 15 line, ATCC # CCL-33) are grown to a confluent monolayer on Dulbecco's Modified Eagle's Medium (DMEM, Gibco) supplemented with 5% fetal bovine serum (Gibco) at 37° C. The culture medium is poured off, and the monolayer is inoculated with pseudorabies virus (Shope strain). After one hour incubation at 37° C., serum-free DMEM is added, infected monolayers showing maximum cytopathic effect (12–24 hours) are harvested by scraping from the culture dish with a rubber policeman, centrifuging the suspension at 3,000 rpm at 4° for 10 minutes, and discarding the supernatant medium. The cell pellet is suspended in 4 times its volume of Tris buffer (0.01M Tris(hydroxymethyl)aminomethane-HCl, ethylene-diamine tetraacetate, pH 7.4) plus 0.5% Triton X-100 (Rohm and Haas). The cell suspension is stirred on a magnetic stirrer at 4° for one and a half hours, during which time the viral envelope is solubilized and floats on the surface of the solution. The solution is then centrifuged at 4° C. for 60 minutes at 10,000 rpm. The supernatant fluid is decanted from the pelleted cellular debris. Each batch is checked for activity in the radial immunodiffusion enzyme-linked assay test, at a dilution of from 1:50 to 1:2000. The optimal concentration is empirically determined as the highest dilution that will, when used in the test, give rapidly developing rings with sharp edges. Most batches give optimal results at a dilution from 1:100 to 1:1000. The antigen preparation is stored at −70° C. until use.

EXAMPLE 2

Preparation of the test plates

Antigen preparation produced according to Example 1 is diluted to 1:500 in coating buffer (0.1M NaHCO$_3$+0.05M Na$_2$CO$_3$, pH 9.6). 60 mm polystyrene test dishes are prewashed with 95% ethanol for 10 minutes and placed on a level surface. After drying, 3 ml of the antigen preparation is pipetted into each dish and allowed to adsorb for 2 to 4 hours at room temperature. The excess is poured off and 3 ml of 1% bovine serum albumin (Sigma) in phosphate buffered saline (PBS) (Gibco) added. After 20 minutes the excess is poured off. A 1% agar (Difco purified) in PBS solution is heated until melted and 6 ml are added to each dish. After the agar solidifies, 2 mm diameter holes are punched out of the solid agar and the dishes covered until use and stored at 4° C.

EXAMPLE 3

Procedure for testing

Animal to be tested is pricked on the ear with a stylet. A drop of blood is drawn into a heparinized capillary tube with a marking of 15 $\mu$l and 15 $\mu$l of the blood is added to a well of each dish. Positive and negative controls are provided to be run with each set of tests. After addition of the blood, the dishes are covered with lids and kept at room temperature for 17 hours.

The agar is stripped from the dish by lifting one edge and then peeling the agar off. The dish is washed three times for 2 or 3 minutes by carefully adding 5 to 10 ml of washing solution (PBS+0.5% Tween-20 (Sigma)) to the edge of the dish, swirling gently over the surface, and carefully pouring it off. Conjugate is prepared by mixing one vial of the anti-swine immunoglobulin conjugated to horseradish peroxidase with 15 ml of washing buffer. The amount of conjugate supplied in the vial is empirically determined to be the least amount that, when mixed with 15 ml of diluent and used in the test, will result in rapidly developing rings with sharp edges, against an acceptable contrasting background. 3 ml of this solution is added to each dish and binding allowed to proceed for 45–60 minutes. The timing of this step is not critical, as intensity but not diameter of the resulting rings will be affected. While the dishes are incubating, 25 ml of 1% agar in PBS is melted and cooled until it is just slightly warm to the touch. The conjugate is poured off slowly and the dish washed as above. Substrate (to give a final concentration of 0.08% aminosalicylic acid and 0.05% $H_2O_2$) is added to the agar solution and mixed quickly. 5 ml of the solution is added immediately to the dish. The agar is allowed to solidify and the color to develop. The rings are dark enough to measure within ten minutes. Longer time will give darker but not larger rings. The serum titer of the test animal is determined by measuring the diameter of the rings and comparing each to the standard reference table provided.

It is apparent that many modifications and variations of this invention as hereinbefore set forth may be made without departing from the spirit and scope thereof. The specific embodiments described are given by way of example only, and the invention is limited only by the terms of the appended claims.

I claim:

1. A method of diagnosing pseudorabies in animals by detecting antibodies to pseudorabies virus which comprises:
   (A) placing a sample of blood or blood serum drawn from an animal in the sample well of a test plate comprising:
      (1) a receptacle having a flat supporting surface,
      (2) a coating adsorbed on said surface of solubilized non-infectious swine pseudorabies virus antigen, said coating including an adhesion promoting carbonate coating buffer,
      (3) a layer of agar overlying said antigen coating, and
      (4 at least one sample receiving well extending through the agar layer,
   (B) incubating said samples to bind antibodies from the sample to the antigen layer,
   (C) removing the agar layer and washing the antigen layer with bound pseudorabies virus antibodies,
   (D) applying a conjugate, an enzyme conjugated anti-swine immunoglobulin, to said bound antibodies, incubating to bind the conjugate to the antibodies, and washing to remove excess conjugate,
   (E) applying an agar layer containing a color producing substrate for the enzyme of the conjugate over the bound conjugate,
   (F) visually measuring the diameter of the resulting colored reaction zone and comparing with a table of standard values.

2. A method according to claim 1 wherein incubation is carried out at room temperature.

3. A method according to claim 1 wherein said sample in the sample well is incubated at room temperature for about 12 to 24 hours.

4. A method according to claim 1 wherein said sample in the sample well is blood and is incubated at room temperature for about 17 hours.

5. A method according to claim 1 wherein said sample in the sample well is blood serum and is incubated at room temperature for about 15 hours.

6. A method according to claim 1 wherein said applied conjugate is incubated at room temperature for about 45 minutes to 2 hours.

7. A method according to claim 1 wherein said conjugate is peroxidase conjugated rabbit or goat anti-swine immunoglobulin and said substrate is 5-aminosalicylic acid or p-phenylenediamine with hydrogen peroxide catalyst.

8. A test plate for use in the detection of pseudorabies antibodies which comprises:
   (A) a receptacle having a flat supporting surface,
   (B) a coating adsorbed on said supporting surface of solubilized non-infectious swine pseudorabies virus antigen, said coating including an adhesion promoting carbonate coating buffer,
   (C) a layer of agar overlying said antigen coating,
   (D) at least one sample-receiving well extending through the agar layer, and
   (E) cover means for keeping the test plate clean and moist until time of use.

9. A test plate according to claim 8 wherein the antigen coating includes as a coating buffer a small amount of sodium bicarbonate and sodium carbonate to promote adhesion to the supporting surface.

10. A test plate according to claim 9 wherein said antigen coating includes between about 0.08% and 0.84% sodium bicarbonate and between about 0.11% and 1.06% sodium carbonate.

11. A test plate according to claim 8 wherein said antigen coating includes a protein fixative agent to add shelf life to the test plate.

12. A test plate according to claim 8 wherein a fixation layer of bovine serum albumin is present overlying said antigen coating.

13. A test plate according to claim 8 wherein said test well is between about 1 and 4 mm in diameter.

14. A test plate according to claim 8 wherein said supporting surface is a polystyrene petri dish.

15. A test plate according to claim 8 which comprises:
   (A) a polystyrene supporting surface,
   (B) a coating adsorbed on said polystyrene surface of solubilized non-infectious swine pseudorabies virus antigen including as a coating buffer between about 0.08% and 0.84% sodium bicarbonate and between about 0.11% and 1.06% sodium carbonate, and a protein fixative agent,
   (C) a fixation layer of bovine serum albumin overlying said antigen coating,
   (D) a layer of agar overlying said serum albumin layer,
   (E) a plurality of sample receiving wells between about 1 and 4 mm diameter extending through the agar layer, and (F) cover means for keeping the test plate clean and moist until time of use.

16. A test kit for diagnosing pseudorabies in swine by detecting antibodies to pseudorabies virus, which kit comprises:

(A) at least one test plate comprising:
(1) a receptacle having a flat supporting surface,
(2) a coating adsorbed on said surface of solubilized non-infectious swine pseudorabies virus antigen, said coating including an adhesion promoting coating buffer,
(3) a layer of agar overlying said antigen coating,
(4) at least one sample-receiving well extending through the agar layer, and
(5) cover means for maintaining the test plate clean and moist until time of use, (B) a container of a conjugate, an enzyme conjugated anti-swine immunoglobulin,
(C) a container of agar,
(D) a container of a color producing substrate for the enzyme of said conjugate for incorporation in said agar, and
(E) instructions for use of the kit including a table of standard values for antibody concentrations for interpretation of test results.

17. A test kit according to claim 16 wherein the kit includes containers of positive and negative pseudorabies control serums.

18. A test kit according to claim 16 wherein the kit includes containers of concentrated washing solution and conjugate diluent.

19. A test kit according to claim 16 for testing 24 samples along with a positive and negative control including:

(A) 4 antigen coated agar test plates in 60 mm polystyrene petri dishes,
(B) 20 mls concentrated buffered washing solution,
(C) 1 vial of enzyme conjugated anti-swine immunoglobulin,
(D) 25 mls agar,
(E) 1 vial color producing enzyme substrate, and
(F) 1 vial hydrogen peroxide.

* * * * *